United States Patent [19]

Wille et al.

[11] 4,385,812
[45] May 31, 1983

[54] OBJECTIVE LENS COVER ASSEMBLY FOR AN OPERATING MICROSCOPE

[75] Inventors: Michael T. Wille, Redding; Nicholas E. Sachuk, Stamford, both of Conn.

[73] Assignee: Surgikos, Inc., New Brunswick, N.J.

[21] Appl. No.: 230,703

[22] Filed: Feb. 2, 1981

[51] Int. Cl.³ .......................................... G02B 21/00
[52] U.S. Cl. ................................................. 350/587
[58] Field of Search ...................... 350/65, 61, 57, 58, 350/318, 587

[56] References Cited

U.S. PATENT DOCUMENTS 3,796,477  3/1974  Geraci ................................... 350/65
4,266,663  5/1981  Geraci ................................... 350/65

Primary Examiner—Jon W. Henry
Attorney, Agent, or Firm—Bollo & Drumm

[57] ABSTRACT

An objective lens cover assembly for employment in a sterile or nonsterile disposable operating microscope drape. The assembly includes a housing adapted to frictionally engage the objective lens frame of the microscope, and to removably receive a lens cover in positive locking and sealing engagement therewith. The housing includes a circumferential flange for seating the lens cover, and a resilient peripheral portion extending downwardly from said flange for receiving the lens cover. The resilient peripheral portion includes resilient lens cover retaining means including a plurality of inwardly deflectable projections, each having a base face spaced from the circumferential flange to define lens cover retaining slots. When the lens cover is received in the housing, the lens cover deflects the lens cover retaining means outwardly to seat the lens cover in the retaining slots. The lens cover is disengaged from the housing by flexing the lens retaining means outwardly.

19 Claims, 5 Drawing Figures

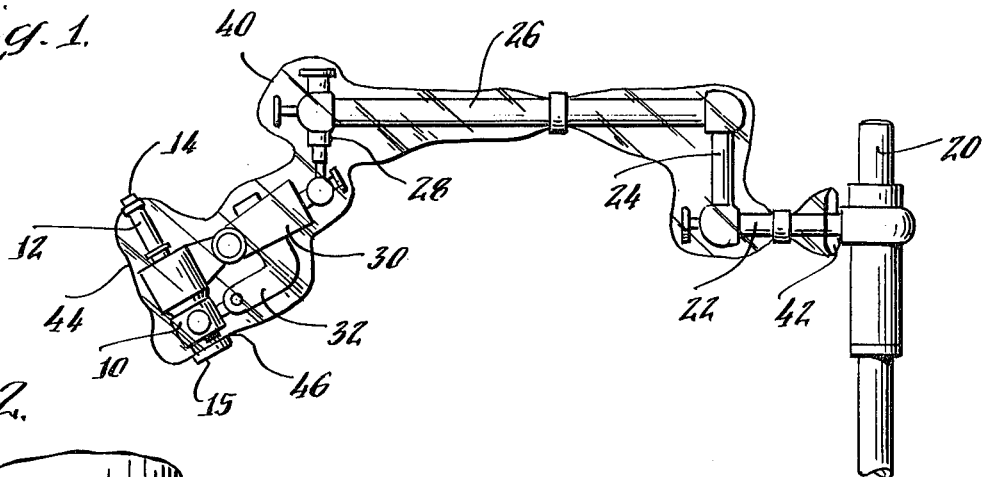
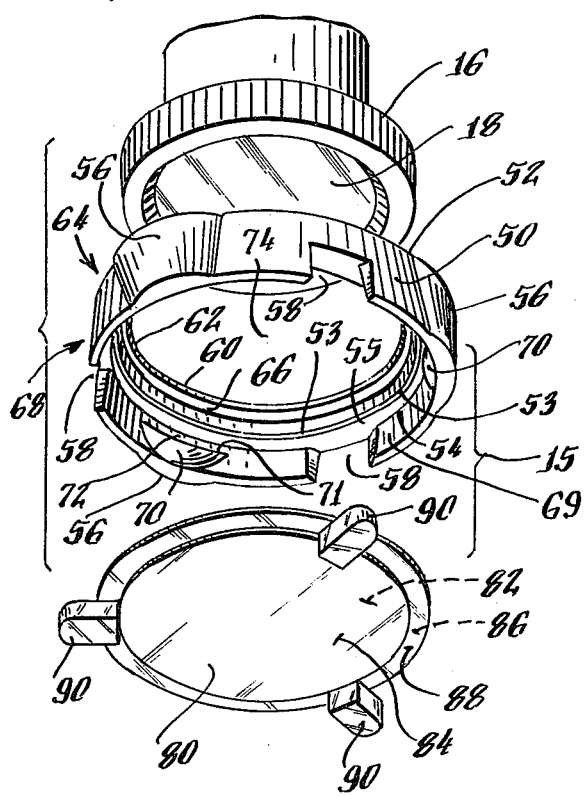
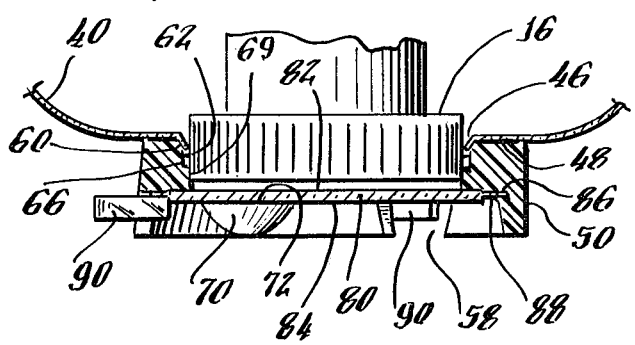
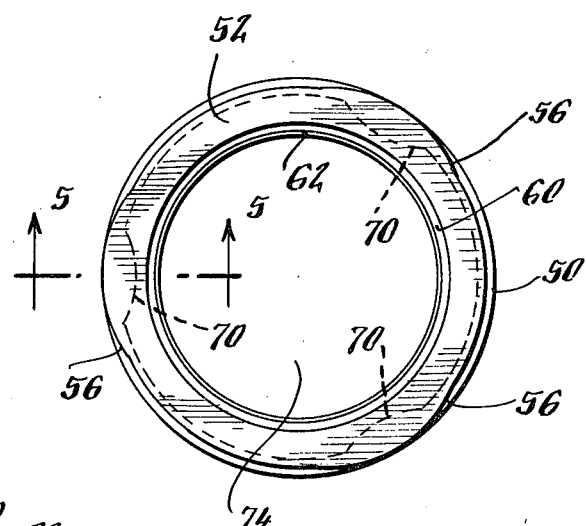
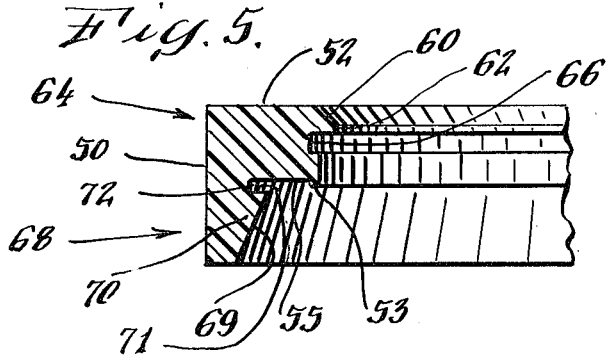

OBJECTIVE LENS COVER ASSEMBLY FOR AN OPERATING MICROSCOPE

BACKGROUND OF THE INVENTION

1. Field of Invention

This invention relates generally to microscope lens cover assemblies, and more specifically to objective lens cover assemblies employed in conjunction with disposable sterile and nonsterile operating microscope drapes.

2. Description of the Prior Art

Operating microscopes are employed in the performance of various surgical procedures. During the performance of such procedures it is necessary to maintain the microscope and surgical field in sterile condition. Difficulty in maintaining sterility is presented by the need to position the microscope objective lens in close proximity to the surgical site. During the performance of surgical procedures the objective lens can become smeared with matter from or near the surgical site. In particular, the lens may become splattered with blood, bone fragments or other solutions introduced into the operating site. Additionally, surgical instruments may contact the objective lens surface scratching or damaging the lens.

Prior art devices have generally provided sterile drape assemblies fabricated of a plastic material to completely house the microscope and microscope support structures. These devices include objective lens cover assemblies of various configurations. However, none of these prior art lens cover assemblies have proved to be entirely satisfactory.

U.S. Pat. No. 3,528,720 to Treace discloses a clear plastic envelope enclosure adapted to be removably fitted over a cantilever supported operating microscope. The drape includes a circular aperture positioned to receive the objective lens of the operating microscope, and an objective lens ring adapted to frictionally engage the objective lens frame. The ring is fabricated of a slightly resilient deformable plastic material. Structurally, the ring includes an annular body frusto-conical in form for engaging the objective lens frame. The upper circumferential portion of the annular body is provided with an external flange for securing the ring to the drape. The lower circumferential portion of the annular body is provided with a circumferential inwardly directed flange which serves as a guard means for protecting the objective lens. Treace does not disclose a means for enclosing the objective lens of the microscope. The bottom of the annular body of the Treace device is open. Fundamentally, the Treace device provides a guard means for protecting the objective lens from damage by hand held surgical instruments (col. 4, lines 64-71). The open lens ring presents the danger that the microscope objective lens will render the surgical field unsterile. Additionally, difficulties arise when matter from the surgical field smears the objective lens.

U.S. Pat. No. 3,698,791 to Walchle et al. discloses a sterile operating microscope drape including an integral lens panel secured in an associated lens housing. The lens housing frictionally receives the objective lens through an aperture in the drape. The lens cover and housing cannot be disassociated from the drape. In cases in which it is necessary to remove the lens cover, the entire drape must be removed.

U.S. Pat. No. 3,796,477, to Geracci discloses a lens ring housing and cover assembly including a resilient lens housing adapted to frictionally receive the objective lens and lens ring of an operating microscope, and a removable lens cover. The lens housing includes an inner circumferential groove for receiving the outer peripheral portions of the lens cover, an annular glare shield, and a recess extending outwardly from the inner to the outer walls of the housing. The lens cover includes an outwardly extending manipulative handle which is received in the recess for disassociating the lens cover from the housing by pulling downwardly on the lens handle. Geracci does not provide a structure which readily facilitates the substitution of replacement lens covers during the progress of operative procedures should the same become necessary.

BRIEF SUMMARY OF THE INVENTION

It is an object of the present invention to provide a disposable objective lens cover assembly for engaging the objective lens frame of an operating microscope in which the lens cover may be readily associated and disassociated from the lens cover housing, while the housing is operatively associated with the objective lens frame of the microscope.

Another object of the present invention is to provide a lens cover assembly wherein the lens cover is positively locked and sealingly engaged in the lens housing.

Another object of the present invention is to provide a lens cover assembly wherein color subtractive lenses may be employed in the lens cover housing.

A further object of this invention is to provide a lens cover assembly which may be fabricated conveniently, inexpensively, but which retains its structural durability in application.

In the present invention, these purposes, as well as others which will be apparent, are achieved generally by provision of an objective lens cover assembly including an optically transparent lens cover and associated lens cover housing. The housing includes an annular opening therethrough from a top end to a bottom end, the top end including resilient wall portions adapted for engaging the objective lens frame of the microscope, the botton end including a circumferential flange, and a resilient peripheral portion extending downwardly from the flange for receiving the lens cover. The resilient peripheral portion includes resilient lens cover retaining means including a plurality of inwardly deflectable projections, each of the projections having a face spaced from the circumferential flange to define lens cover retaining slots. When the lens cover is received in the housing and moved towards the circumferential flange, the lens cover deflects the deflectable projections outwardly. When the lens cover passes below the base faces of the deflectable projections, the deflectable projections deflect inwardly to overlie portions of lens cover, thereby locking the lens cover in the lens cover retaining slots, and sealingly seating the lens cover against the circumferential flange. The lens cover may be readily disengaged from the housing by flexing the deflectable projections outwardly.

It should be understood that the term "optically transparent" as used in this specification and the appended claims includes lenses which are clear, colored, polarized, those having different wavelength sensitivities, those that are optically distorting, and lenses having a matrix pattern.

In the preferred embodiment, the lens cover is provided with a peripheral lens handle means, and the housing is provided with a lens handle opening. The lens handle means is employed to guide the lens cover during assembly and disassembly from the lens housing, thus obviating the need to contact the lens cover surfaces. Advantageously, the top and bottom surfaces of the lens cover are provided with peripheral circumferential recess areas so that the lens cover may be pivotally seated in the housing.

An objective lens cover assembly fabricated in accordance with this invention is adapted to be employed in sterile and nonsterile operative procedures. When operating conditions require a localized sterile condition immediately adjacent the observed surgical field, the objective lens cover assembly may be employed independently to provide a sterile condition at the objective lens of the microscope. When sterile conditions are required in a broader environment, the objective lens cover assembly of this invention may be employed in conjunction with a disposable operating microscope drape.

Other objects, aspects and advantages of the present invention will be apparent when the detailed description of the preferred embodiment of the invention is considered in conjunction with the drawings, which should be construed in an illustrative and not a limiting sense, as follows:

DESCRIPTION OF THE DRAWINGS

FIG. 1 is a schematic side view of a conventional operating microscope operatively associated with a sterile disposable drape in combination with a lens cover assembly in accordance with the present invention.

FIG. 2 is a perspective view of the lens housing and lens cover disassociated from a portion of the microscope objective lens and associated lens frame.

FIG. 3 is a transverse sectional view through the housing and lens cover operatively associated with the objective lens and objective lens frame.

FIG. 4 is a top plan view of the lens cover housing.

FIG. 5 is a sectional view of the lens housing taken on line 5—5 of FIG. 4.

DESCRIPTION OF THE PREFERRED EMBODIMENTS

Referring to FIGS. 1, 2, and 3, a conventional operating microscope is illustrated generally as 10 associated with the lens cover assembly 15 and microscope drape 40 operatively engaged to the objective lens 18 and frame 16 of the microscope 10. The microscope 10 is adjustably mounted relative to a cantilever or support means 20 by means of support arm members including 22, 24, 26, 28, 30 and 32. The microscope drape 40 is fabricated from a heat-resistant plastic adapted to completely house the microscope 10 and supporting arm so that no air can escape from the microscope 10 except through an open end 42 remote from the microscope 10. The drape 40 is provided with a tubular extension 44 for enclosing the microscope ocular 12. The drape 40 includes means for securing the tubular extension 44 to the microscope eyepiece 14 to preclude the escape of air from the interior of drape 40. The drape 40 is also provided with an aperture 46 through which the objective lens frame 16 is received. When the microscope 10 is provided with observer arms (not shown), the drape 40 may be provided with tubular extensions and associated securing means, for enclosing the observer arms. As illustrated in FIG. 3 the drape 40 is secured by an adhesive 48 to the top end surface 52 of the lens cover housing 50.

Referring to FIG. 2, there is illustrated the objective lens cover assembly 15 of this invention disassembled from the objective lens 18 and objective lens frame 16 of the microscope 10. The objective lens cover assembly 15 includes optically transparent lens cover 80 and an associated lens cover housing 50. The housing is fabricated of a flexible and resilient material, such as for example, thermoplastic rubber. The housing 50 includes an annular opening 74 therethrough from a top end 52 to a bottom end 54, the top end 52 including resilient wall portions 64 adapted for engaging the objective lens 18 and objective lens frame 16 of the microscope 10, the bottom end 54 including a circumferential flange 55, and a resilient peripheral portion 68 extending downwardly from the circumferential flange 55 for receiving the lens cover 80. The housing 50 also includes a support means which comprises three thickened resilient exterior wall members 56 appended to the resilient wall portions 64 and the resilient peripheral portion 68.

Referring to FIGS. 2 and 5, the resilient peripheral portion 68 includes resilient lens cover retaining means including a plurality of deflectable projections 70, each having a base face 71 spaced from the circumferential flange 55 to define lens cover retaining slots 72. In the preferred embodiment the lens retaining means includes three deflectable projections 70. The resilient peripheral portion 68 is provided with an internal surface 69 disposed angularly outwardly to shield the objective lens 18 from glare and reflected light originating outside the operating field, and to permit unobstructed entry of the lens cover 80.

The circumferential flange 55 is provided with a downwardly projecting circumferential rib 53. When the lens cover 80 is operatively positioned in the housing 50, the lens cover 80 is biased against the base faces 71 of the lens retaining means. This arrangement achieves sealing engagement of the lens cover 80 against the circumferential flange 55.

Referring to FIGS. 4 and 5, the resilient wall portions 64 include a circumferential rim 60 projecting angularly outwardly into the top end 52 of the housing 50 to permit unobstructed engagement of the objective lens frame 16, a circumferential lip 62 appended to the rim 60, and circumferential groove 66 subjacent to the circumferential lip 62. As can be seen in FIG. 3, when the housing 50 engages the objective lens frame 16, the circumferential lip 62 is received in the circumferential groove 66, thereby biasing the objective lens frame 16 in the housing 50.

As illustrated in FIG. 2, the lens cover 80 includes top and bottom surfaces 82 and 84, and an appended handle means comprising three peripheral handles 90 extending outwardly from the bottom surface 84 of the lens cover 80. In order to accommodate the peripheral handles 90, the resilient peripheral portion 68 of the housing 50 is provided with handle openings 58. The handle means 90 are employed to guide the lens cover 80 during assembly and disassembly of the lens cover 80 from the lens housing 50, thereby obviating the need to contact the top and bottom surfaces 82 and 84 of the lens cover 80. In the preferred embodiment, the top and bottom surfaces 82 and 84 of the lens cover 80 are also provided with peripheral circumferential recess areas 86 and 88. The handle openings 58 are wider in cross-section than the handles 90 so that the lens cover 80 may be pivotally seated in the housing 50. The lens cover 80 is fabricated of an optically transparent material, such as acrylic. In the preferred embodiment the lens cover 80 employed is approximately 1/16" thick.

Referring to FIG. 3, the lens cover assembly 15 of this invention is shown operatively engaged to the microscope objective lens frame 16. As can be seen with reference to FIGS. 4 and 5, upon frictional engagement of the objective lens frame 16 and lens cover assembly 15, the objective lens frame 16 contacts the circumferential rim 60 without obstruction causing the circumferential lip 62 to deflect into the circumferential groove 66, thereby frictionally biasing the objective lens frame 16 in the housing 50.

As illustrated in FIGS. 3 and 5, the lens cover 80 may be readily associated into and disassociated from the housing 50. When the lens cover 80 is received in the housing 50 and moved towards the circumferential flange 55, the lens cover 80 deflects the deflectable projections 70 outwardly. When the lens cover 80 passes below the base faces 71 of the deflectable projections 70, the deflectable projections 70 deflect inwardly to overlie portions of the lens cover 80 circumferential recess area 88, thereby locking the lens cover 80 in the lens cover retaining slot 72, and sealingly seating the lens cover against the circumferential flange 55. The lens cover 80 may be readily disengaged from the housing 50 by flexing the deflectable projections outwardly.

Advantageously, the associability and disassociability of the lens cover 80 permits the maintenance of sterility in the operating field. When necessary the lens cover 80 may be replaced during the course of an operative procedure. For this purpose the drape 40 is secured to the top end 52 of the housing 50 by adhesive 48, to achieve an airtight association between the objective lens 18, objective lens frame 16, and the drape 40.

The objective lens assembly 15 of this invention provides an additional advantage in that the lens housing 50 may be employed with color subtractive lenses adapted for application in the lens housing 50. Color subtractive lenses are employed in microsurgical procedures. When the surgical site is viewed through color subtractive lenses, the visual appearance of certain components within the surgical site are enhanced or diminished. This ability facilitates both initial and constant identification of relatively small structures during surgical procedures. The subtractive primary colors (cyan, magenta, and yellow), and the additive primary colors (red, green and blue) are employed to enhance or diminish certain colors in the surgical site to achieve the desired visual effect. As will be appreciated by those skilled in the art, the ability to either enhance or diminish certain colors in the surgical site has become increasingly important in the performance of delicate surgical procedures under magnification. It will also be apparent that the housing 50 when employed in conjunction with color subtractive lenses provides efficiencies in operation and economy.

It should be understood that the lens cover assembly 15 of this invention may be employed independently, if desired, or in conjunction with the disposable operating microscope drape 40. It is, of course, understood that the lens cover assembly 15 whether employed separately or in conjunction with the drape 40 may be provided in a sterile package.

It should be understood by those skilled in the art that various modifications may be made in the present invention, without departing from the spirit and scope thereof as described in the specifications and defined in the appended claims.

What is claimed is:

1. An objective lens cover assembly for use with a disposable operating microscope drape, the objective lens cover assembly being adapted to engage the objective lens frame of a microscope, comprising:
   an optically transparent lens cover;
   a housing having a annular opening there through from a top end to a bottom end;
   said top end including resilient wall portions adapted for engaging the objective lens frame of the microscope;
   said bottom end including a circumferential flange, and a resilient peripheral portion extending downwardly from said circumferential flange, for receiving said optically transparent lens cover, said circumferential flange also including a circumferential rib extending downwardly therefrom and spaced from said resilient peripheral portion;
   said resilient peripheral portion including resilient lens cover retaining means having a plurality of deflectable projections;
   each of said deflectable projections having a base face spaced from said circumferential flange to define lens cover retaining slots therebetween for receiving said optically transparent lens cover therein, when said deflectable projections are deflected outwardly by movement of said optically transparent lens cover toward said circumferential flange, said plurality of deflectable projections being equally spaced about said resilient peripheral portion with each of said base faces dimensioned to occupy only a portion of the periphery of said resilient peripheral portion;
   said deflectable projections deflecting inwardly to overlie portions of said optically transparent lens cover when said optically transparent lens cover passes below said base faces of said deflectable projections, thereby positively locking said optically transparent lens cover in the lens cover retaining slots and sealingly seating said lens cover against said circumferential flange and said circumferential rib, while enabling said optically transparent lens cover to be readily disengaged from said housing by flexing said deflectable projections outwardly.

2. The objective lens cover assembly of claim 1, wherein:
   said housing is employed in conjunction with a color subtractive optically transparent lens cover.

3. An objective lens cover assembly for use with a disposal operating microscope drape, the objective lens cover assembly being adapted to engage the objective lens frame of a microscope, comprising:
   an optically transparent lens cover;
   a housing having an annular opening therethrough from a top end to a bottom end;
   said top end including resilient wall portions adapted for engaging the objective lens frame of the microscope;
   said bottom end including a circumferential flange, and a resilient peripheral portion extending downwardly from said circumferential flange for receiving said optically transparent lens cover;
   said resilient peripheral portion having an internal surface disposed angularly outwardly to shield the objective lens from glare and reflected light originating outside the operating field and to permit unobstructed entry of said optically transparent lens cover, and resilient lens cover retaining means having a plurality of deflectable projections;

each of said deflectable projections having a base face spaced from said circumferential flange to define lens cover retaining slots therebetween for receiving said optically transparent lens cover therein when said deflectable projections are deflected outwardly by movement of said optically transparent lens cover toward said circumferential flange;

said deflectable projections deflecting inwardly to overlie portions of said optically transparent lens cover when said optically transparent lens cover passes below said base faces of said deflectable projections, thereby positively locking said optically transparent lens cover in the lens cover retaining slots and sealingly seating said lens cover against said circumferential flange while enabling said optically transparent lens cover to be readily disengaged from said housing by flexing said deflectable projections outwardly.

4. The objective lens cover assembly of claim 3, wherein:

said top end includes, a circumferential rim projecting angularly outwardly into the top end of the housing to permit unobstructed engagement of the objective lens frame, a circumferential lip appended to said rim, and a circumferential groove subjacent to said lip so that when said housing engages the objective lens frame, said lip is received in said circumferential groove, thereby frictionally biasing said lens frame in said housing.

5. The objective lens cover assembly of claim 4, wherein:

said housing includes support means for strengthening the flexure of said lens retaining means.

6. The objective lens cover assembly of claim 5, wherein:

said circumferential flange includes a downwardly projecting circumferential rib, so that when said lens cover is operatively positioned in said housing, said lens cover is biased against said base face of said lens retaining means, thereby sealingly engaging said lens cover against said circumferential flange.

7. The objective lens cover assembly of claim 6, wherein:

said lens retaining means comprises three inwardly deflectable projections, each of said projections having a base face spaced from said circumferential flange to define three lens cover retaining slots.

8. The objective lens cover assembly of claim 7, wherein:

said housing is fabricated of thermoplastic rubber.

9. The objective lens cover assembly of claim 8, wherein:

said lens cover is fabricated of acrylic.

10. An objective lens cover assembly for use with a disposable operating microscope drape, the objective lens cover assembly being adapted to engage the objective lens frame of the microscope, comprising:

an optically transparent lens cover having bottom and top surfaces including handle means having three peripheral handles extending outwardly from said bottom lens cover surface;

said top and bottom lens cover surfaces each having peripheral circumferential recess areas;

a lens housing for receiving said optically transparent lens cover, said lens housing including top and bottom ends;

said top end including resilient wall portions adapted for engaging the objective lens frame of the microscope;

said bottom end including a circumferential flange and a resilient peripheral portion extending downwardly from said flange for receiving said lens cover;

said resilient peripheral portion including three handle openings wider in cross-section than said handles, so that said lens cover may be pivotally seated in said lens housing;

said resilient peripheral portion including resilient lens cover retaining means including a plurality of deflectable projections;

each of said deflectable projections having a base face spaced from said circumferential flange to define lens cover retaining slots therebetween for receiving said optically transparent lens cover therein when said deflectable projections are delfected outwardly by movement of said optically transparent lens cover toward said circumferential flange;

said deflectable projections deflecting inwardly to overlie portions of said optically transparent lens cover when said optically transparent lens cover passes below said base faces of said deflectable projections, thereby positively locking said optically transparent lens cover in the lens cover retaining slots and sealingly seating said lens cover against said circumferential flange, while enabling said optically transparent lens cover to be readily disengaged from said lens housing by flexing said deflectable projections outwardly;

said handles being employed to guide said lens cover during assembly and disassembly from said lens housing, thus obviating the need to contact said lens cover surfaces.

11. The objective lens cover assembly of claim 10, wherein:

said resilient peripheral portion has an internal surface disposed angularly outwardly to shield the objective lens from glare and reflected light originating outside the operating field, and to permit unobstructed entry of said lens cover.

12. The objective lens cover assembly of claim 11, wherein:

said resilient wall portions includes, a circumferential rim projecting angularly outwardly into the top end of the housing to permit unobstructed engagement of the objective lens frame, a circumferential lip appended to said rim, and a circumferential groove subjacent to said lip, so that when said housing engages the objective lens frame, said lip is received in said circumferential groove, thereby frictionally biasing said lens frame in said housing.

13. The objective lens cover assembly of claim 12, wherein:

said housing includes support means for strengthening the flexure of said lens retaining means, said support means including a thickened resilient exterior housing wall member integrally appended to said resilient wall portions and said resilient peripheral portion.

14. The objective lens cover assembly of claim 13, wherein:

said circumferential flange includes a downwardly projecting circumferential rib, so that when said lens cover is operatively positioned in said housing, said lens cover is biased against said base faces of said deflectable projections, thereby sealingly engaging said lens cover against said circumferential flange.

15. The objective lens cover assembly of claim 14, wherein:
said lens retaining means comprises three inwardly deflectable projections, each of said projections having a base face spaced from said circumferential flange to define three lens cover retaining slots.

16. The objective lens cover assembly of claim 15, wherein:
said housing is fabricated of thermoplastic rubber.

17. The objective lens cover assembly of claim 16, wherein:
said lens cover is fabricated of acrylic.

18. An objective lens cover for use with a disposable operating microscope drape, the objective lens cover assembly being adapted to engage the objective lens frame of the microscope, comprising:
an optically transparent lens cover having bottom and top surfaces including handle means appended to the periphery of said lens cover;
a lens housing for receiving said optically transparent lens cover, said lens housing including top and bottom ends;
said top end including resilient wall portions adapted for engaging the objective lens frame of the microscope;
said bottom end including a circumferential flange, and a resilient peripheral portion extending downwardly from said flange for receiving said lens cover;
said resilient peripheral portion including resilient lens cover retaining means including a plurality of deflectable projections;
each of said deflectable projections having a base face spaced from said circumferential flange to define lens cover retaining slots therebetween for receiving said optically transparent lens cover therein when said deflectable projections are deflected outwardly by movement of said optically transparent lens cover toward said circumferential flange;
said deflectable projections deflecting inwardly to overlie portions of said optically transparent lens cover when said optically transparent lens cover passes below said base faces of said deflectable projections, thereby positively locking said optically transparent lens cover in the lens cover retaining slots, and sealingly seating said lens cover against said circumferential flange, while enabling said optically transparent lens cover to be readily disengaged from said housing by flexing said deflectable projections outwardly;
said resilient peripheral portion including lens handle openings adapted to receive said handle means;
said plurality of deflectable projections being equally spaced about said resilient peripheral portion between said lens handle openings, each of said base faces of said deflection projections being dimensioned to occupy only a portion of the distance between said lens handle openings;
said handle means being employed to guide said lens cover during assembly and disassembly from the lens housing, thus obviating the need to contact said lens cover surfaces.

19. The objective lens cover assembly of claim 18, wherein:
said housing is employed in conjunction with a color subtractive optically transparent lens cover.

* * * * *